(12) United States Patent
Morgan

(10) Patent No.: US 9,999,488 B1
(45) Date of Patent: Jun. 19, 2018

(54) DEVICE FOR PROVIDING A MEASURED VERTICAL DIMENSION OF OCCLUSION

(71) Applicant: Todd D Morgan DMD, Inc., Encinitas, CA (US)

(72) Inventor: Todd D. Morgan, Carlsbad, CA (US)

(73) Assignee: TODD D MORGAN DMD, INC., Encinitas, CA (US)

(*) Notice: Subject to any disclaimer, the term of this patent is extended or adjusted under 35 U.S.C. 154(b) by 153 days.

(21) Appl. No.: 14/751,936

(22) Filed: Jun. 26, 2015

Related U.S. Application Data

(60) Provisional application No. 62/023,795, filed on Jul. 11, 2014.

(51) Int. Cl.
| | | |
|---|---|---|
| *A61C 19/05* | (2006.01) | |
| *A61B 5/00* | (2006.01) | |
| *A61F 5/56* | (2006.01) | |
| *A63B 71/08* | (2006.01) | |

(52) U.S. Cl.
CPC ............ *A61C 19/05* (2013.01); *A61B 5/4818* (2013.01); *A61F 5/566* (2013.01); *A63B 71/085* (2013.01); *A63B 2071/086* (2013.01); *A63B 2071/088* (2013.01)

(58) Field of Classification Search
CPC ................. A63B 71/085–71/088; A61F 5/566
See application file for complete search history.

(56) References Cited

U.S. PATENT DOCUMENTS

| | | | | |
|---|---|---|---|---|
| 1,492,561 A | * | 5/1924 | Gabriel | F16B 43/007 301/68 |
| 3,618,214 A | * | 11/1971 | Armstrong | A61C 7/36 267/168 |
| 5,947,724 A | * | 9/1999 | Frantz | A61F 5/566 128/848 |
| 6,109,265 A | * | 8/2000 | Frantz | A61F 5/566 128/848 |

* cited by examiner

*Primary Examiner* — Michael Kahelin
(74) *Attorney, Agent, or Firm* — Sheppard Mullin Richter & Hampton LLP

(57) ABSTRACT

Devices and methods for treating respiratory problems of a subject, such as those related to sleep apnea, are presented herein. An implementation of a device may be configured to provide a measured vertical dimension of occlusion (VDO) and/or mandibular advancement in a subject. Methods for treating a subject through the use of the device may include systematically increasing and/or decreasing the measured VDO provided by the device.

5 Claims, 6 Drawing Sheets

DEVICE FOR PROVIDING A MEASURED VERTICAL DIMENSION OF OCCLUSION

CROSS REFERENCE TO RELATED APPLICATIONS

This application claims the benefit of U.S. Provisional Application Ser. No. 62/023,795, filed Jul. 11, 2014, which is incorporated herein by reference.

FIELD OF THE DISCLOSURE

This disclosure relates to oral appliances used for the treatment of sleep apnea that are configured to provide a predetermined vertical dimension of occlusion.

BACKGROUND

Sleep apnea occurs when a subject periodically stops breathing or has diminished breathing during sleep. Oral appliances may be used in the treatment of sleep apnea. Oral appliances may have a mandibular portion that contacts one or more mandibular teeth of a subject in an as-used position inserted into the mouth of the subject and a maxillary portion that contacts one or more maxillary teeth of the user when in the as-used position. Oral appliances for treatment of sleep apnea may be configured to provide mandibular advancement of the subject for opening obstructions of the subject's upper airway.

SUMMARY

One or more aspects of the disclosure relate to a device for providing a measured vertical dimension of positioning the jaw in a subject. The vertical dimension of a positioning of the jaw may be referred to as "vertical dimension of occlusion" or, "VDO." In some implementations, the device may be employed to modify an oral appliance used for the treatment of sleep apnea. The device may comprise one or more tabs configured to be positioned between contact surfaces of a mandibular portion and a maxillary portion of a wearable oral appliance. An individual tab may be configured to be carried by one or more components of an oral appliance for operative positioning thereon. An individual tab may be formed with a thickness that provides a predetermined displacement of the mandibular portion from the maxillary portion when the oral appliance is worn by a subject.

Another aspect of the disclosure related to an oral appliance device configured to provide a measured VDO in a subject. The device may comprise one or more of a maxillary portion having an upper cavity configured to receive one or more maxillary teeth of a subject, a mandibular portion having a lower cavity configured to receive one or more mandibular teeth of the subject, one or more connectors, one or more tabs configured to be positioned between contact surfaces of the mandibular portion and the maxillary portion, and/or other components. A given connector may have a first end configured for attachment to a part of a maxillary portion and a second end configured for attachment to a part of a mandibular portion. A given connector may be configured to advance the mandibular portion forward of the maxillary portion. The forward advancement may be configured to provide mandibular advancement for the wearer of the device. An individual tab may be formed with a predetermined thickness that may provide a predetermined displacement of the mandibular portion from the maxillary portion when operatively positioned on the device. An individual tab may be configured for attachment to the mandibular portion such that the mandibular portion may carry the tab and/or facilitate an operative positioning thereon. The device may be used for the systematic treatment of sleep apnea sufferers and/or other respiratory ailments.

These and other features and characteristics of the present technology, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION

Figure 1:
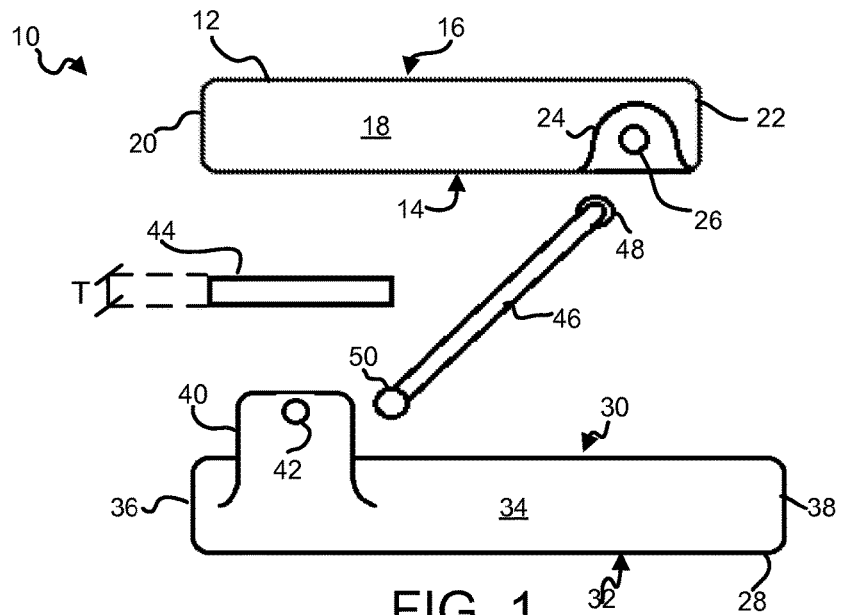
FIG. 1 illustrates an exploded side view of a device configured to provide a measured VDO, in accordance with one or more implementations.

FIG. 1 illustrates an implementation of a device 10 configured to provide a measured vertical dimension of occlusion (VDO). VDO may refer to a measure of displacement of the maxilla and the mandible of a subject when the maxillary teeth and the mandibular teeth are engaged within an oral appliance. By way of non-limiting example, a Mandibular Repositioning Device (MRD) and/or other types of devices may be configured to hold the mandible forward in relationship to the maxilla. The device 10 described herein may be used for treating subjects suffering from sleep apnea and/or other respiratory problems. For example, the device 10 be employed as an oral appliance, and/or components of the device 10 may be used to modify existing oral appliance, to provide systemic application of vertical dimension of occlusion for sleep apnea and/or other medical issues.

In one or more implementations, the device 10 may be a wearable oral appliance configured to be inserted into a mouth of a subject in an as-used position. The device 10 may be configured to provide a predetermined amount of mandibular advancement for a subject wearing the device 10. In some implementations, mandibular advancement (positioning the jaw forward) may facilitate displacing a subject's tongue forward in the mouth. By positioning the tongue in a forward position, the pharyngeal airway of the subject may be substantially opened and/or made less obstructed as to reduce the occurrence of sleep apnea related respiratory problems. One or more implementations of the device 10 may facilitate the addition and/or modification of a measured VDO. A given VDO may facilitate further increasing an opening of the pharyngeal airway and/or other advantages. A given VDO may facilitate one or more of a further reduction of respiratory problems, improved comfort of the subject wearing the device 10, and/or other advantages.

Figure 2:
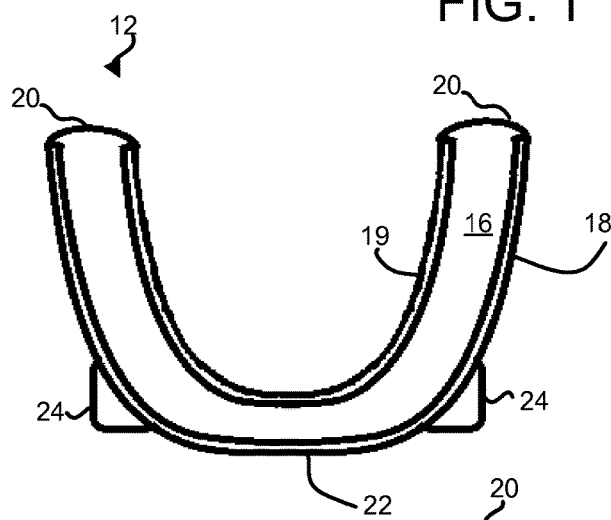
FIG. 2 illustrates a top view of a maxillary portion of the device of FIG. 1, in accordance with one or more implementations.
Figure 3:
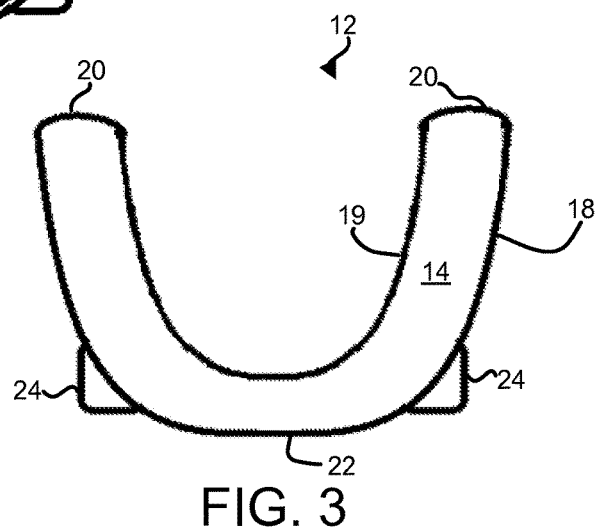
FIG. 3 illustrates a bottom view of the maxillary portion of the device if FIG. 1, in accordance with one or more implementations.

In some implementations, the device 10 may include one or more of a maxillary portion 12, a mandibular portion 28, one or more connectors 46, one or more tabs 44 for providing a VDO, and/or other components (it is noted that the opposite side of the device 10 as that shown in FIG. 1 may be a mirror image than that shown in FIG. 1, employing one or more like components). As shown in FIG. 1, FIG. 2, and FIG. 3, the maxillary portion 12 may comprise one or more of a substantially U-shaped body, and/or other components. The maxillary portion 12 may be formed from one or more materials used in dentistry and/or other fields. By way of non-limiting example, the maxillary portion 12 may be formed from one or more of methyl methacrylate compounds, carbon and nylon based polymers, and/or other materials.

In some implementations, the maxillary portion 12 may be configured to receive at least some of the maxillary teeth of a subject for attaching the device 10 in the as-used position inserted into the mouth of the subject. The maxillary portion 12 may include one or more of a contact surface 14, an upper cavity 16 being opposite the contact surface 14, one or more proximal ends 20, and/or a distal end 22. The upper cavity 16 may be configured to receive and/or otherwise engage at least some of the maxillary teeth of a subject. In some implementations, receiving at least some of the maxillary teeth of a subject may comprise seating the at least some of the maxillary teeth within the upper cavity 16 and/or other techniques for receiving teeth in the upper cavity 16. The upper cavity 16 may be formed by one or more of an outer sidewall 18, an inner sidewall 19, and/or by other components of the maxillary portion 12. In some implementations, the maxillary portion 12, upper cavity 16, and/or other portions of the upper cavity 16 (e.g., a liner disposed within the cavity, and/or other components, not shown in FIGS. 1-3) may be formed of material configured to be molded and/or otherwise fitted to the teeth of the subject. Such material may include one or more of thermally responsive materials, plastics, polymers, and/or other materials. A thermally responsive material may comprise a material that, when heated (e.g., submerged in hot water and/or heated in other ways), the material may soften, and when placed in a mouth of a subject and the subject bites down, the thermally responsive material may directly form to and/or around the subjects teeth and/or gums. The processes of forming a thermally responsive material to a subject's teeth and/or gums may be referred to as a 'boil-and-bite' process and/or other terms. When cooled, the thermally responsive material may set and/or retrain an impression of the subject's teeth and mouth. For example, a thermally responsive material may comprise one or more of a soft acrylic, silicone, ethylene vinyl acetate, a thermal-forming polymer, and/or other materials.

In some implementations, the upper cavity 16 may be formed to the shape and/or configuration of the maxillary teeth and/or gums of a user by other techniques. For example, an impression of the subject's teeth may be taken and used as a mold to form the upper cavity 16.

Figure 6:
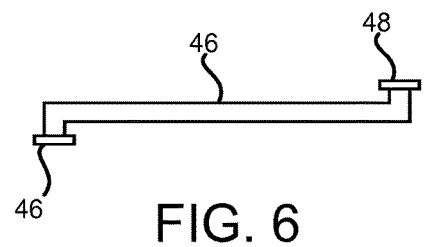
FIG. 6 illustrates a connector configured to provide mandibular advancement that may be configured for use with the device of FIG. 1, in accordance with one or more implementations.

In some implementations, the maxillary portion 12 may include one or more opposing connector mounts 24. The one or more opposing connector mounts 24 may be disposed on opposing sides of the outer sidewall 18 and/or other locations. The one or more opposing connector mounts 24 may be positioned at or near the distal end 22 and/or other locations. The connector mounts 24 may be used for attaching the connector 46 between the maxillary portion 12 and the mandibular portion 28. An attachment of the connector 46 between the maxillary portion 12 and mandibular portion 28 may be configured to provide mandibular advancement (e.g., the mandibular portion 28 may be maintained at a forward position relative to the maxillary portion 12 via the connector 46). The connector mounts 24 may include a receiving aperture 26 and/or other components configured to receive a first end 48 of the connector 46 and/or to attach it thereto. In some implementations, the attachment of the first end 48 of the connector 46 to the aperture 26 may be one or more of rotatable, fixed, and/or other types of attachment. By way of non-limiting example, in some implementations, the first end 48 may include a pin with a flanged end (see, e.g., FIG. 6). The pin with the flanged end may be configured to lock and/or otherwise securely attached the first end 48 within the aperture 26. The use of the aperture 26 and pin with flanged end of the connector 46 is provided merely for illustrative purposes and is not intended to be limiting. In some implementations, other techniques for attaching the connector 46 to the maxillary portion 12 may be employed to achieve a desired attachment type.

Figure 4:
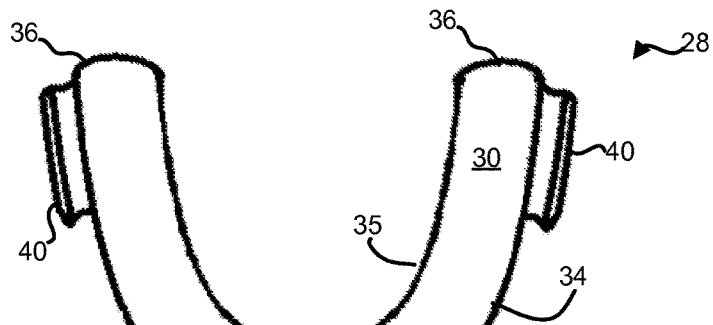
FIG. 4 illustrates a top view of a mandibular portion of the device of FIG. 1, in accordance with one or more implementations.
Figure 5:
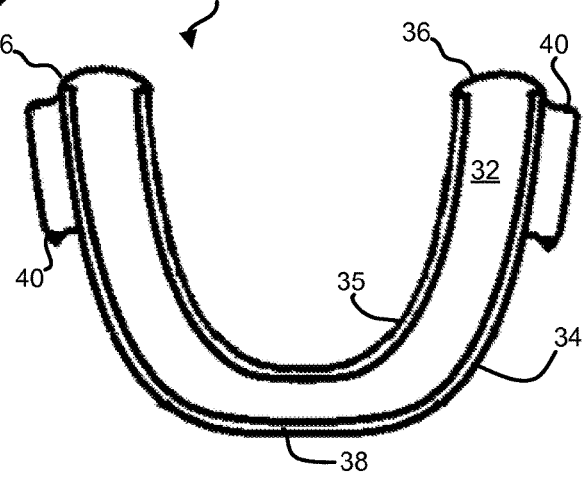
FIG. 5 illustrates a bottom view of the mandibular portion of the device of FIG. 1, in accordance with one or more implementations.

Referring now to FIG. 1, FIG. 4, and FIG. 5, the mandibular portion 28 may comprise a substantially U-shaped body, and/or other components. The mandibular portion 28 may be formed the same or similar to the maxillary portion 12. The mandibular portion 28 may be configured to receive at least some of the mandibular teeth of a subject to facilitate attachment of the device 10 within the mouth of the subject in the as-used position.

The mandibular portion 28 may include one or more of a contact surface 30, a lower cavity 32 being opposite the contact surface 30, one or more proximal ends 36, a distal end 38, and/or other components. The lower cavity 32 may be configured to receive and/or otherwise engage at least some of the mandibular teeth of a subject. Receiving and/or otherwise engaging at least some of the mandibular teeth may comprise seating the mandibular teeth within the lower cavity 32. The lower cavity 32 may be formed by one or more of an outer sidewall 34, an inner sidewall 36, and/or other components. In some implementations, one or more of the mandibular portion 28, lower cavity 32, and/or other portions of the lower cavity 32 (e.g., a liner disposed within the cavity and/or other components, not shown) may be formed of material configured to be molded, formed, and/or otherwise fitted to the teeth of the subject.

The mandibular portion 28 may include one or more opposing connector mounts 40. The one or more opposing connector mounts 40 may be disposed on opposing sides of the outer sidewall 34 and/or other locations. The one or more opposing connector mounts 40 may be positioned at or near the proximal ends 36. In some implementations, the one or more connector mounts 40 may be configured such that they may project a predetermined distance from the outer sidewall 34. By way of non-limiting example, an individual connector mount 40 may form a "wing" and/or other shape extending from the outer sidewall 34. The one or more connector mounts 40 may be configured to facilitate attachment of a connector 46 between the maxillary portion 12 and the mandibular portion 28. A given connector mount 40 may include one or more of a receiving aperture 42 configured to receive a second end 50 of the connector 46 to attach it thereto and/or other components. In some implementations, an attachment of the second end 50 of the connector 46 to the aperture 42 may be one or more rotatable, fixed, and/or other types of attachment. In some implementations, the second end 48 may include a pin with a flanged end (see, e.g., FIG. 6) and/or other components. A pin with a flanged end may be configured to lock and/or otherwise securely attach the second end 48 with the aperture 42. In some implementations, an attachment of the second end 48 with the aperture 42 may be removable. The use of the aperture 42 and pin with flanged end of the connector 46 is provided merely for illustrative purposes and is not intended to be limiting. In some implementations, other techniques for attaching the connector 46 to the mandibular portion 28 may be employed. By way of non-limiting example, a mechanical fastener such as screws and/or other mechanical fasteners may be used.

Figure 7:
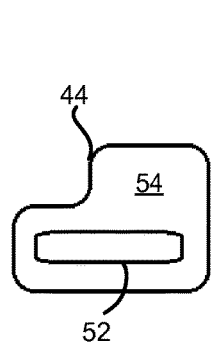
FIG. 7 shows a top view of a tab configured to be carried by a mandibular portion of the device of FIG. 1, in accordance with one or more implementations.
Figure 8:
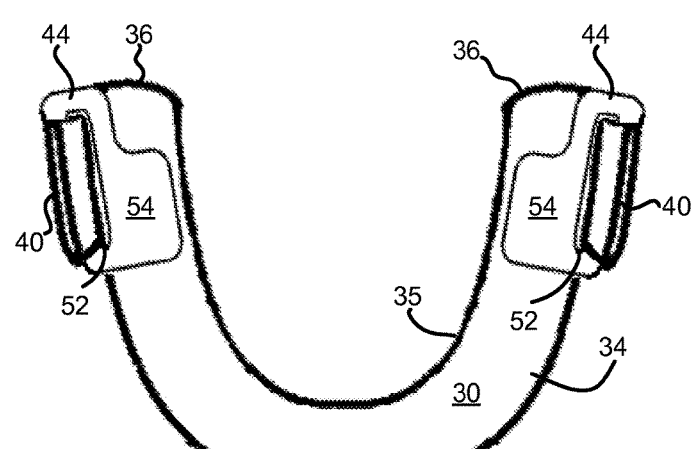
FIG. 8 shows a top view of a mandibular portion of the device of FIG. 1, in accordance with one or more implementations.

Referring now to FIG. 1, FIG. 7, and FIG. 8, a given tab 44 may be configured to provide a measured distance for a VDO of a subject wearing the device 10 in an as-used position. The tab 44 may be formed from a material including one or more of a thermo-forming polymer used in the fabrication of dental prosthetics and/or orthodontic appliances, resilient polymers (e.g., that may provide an amount of "give"), hard polymers, nylon polymers, and/or other materials. The tab 44 may be formed by one or more of injection molding, machining, and/or by other techniques suitable for the intended purpose(s) presented herein. The tab 44 may include one or more of a longitudinal slot 52 configured to facilitate mounting of the tab 44 to a connector mount 44 of the mandibular portion 28, and/or other components. For example, the slot 52 may be sized as a clearance slot and/or other type of slot. The slot 52 may be configured such that the tab 44 may be slid over the connector mount 44 prior to attachment of the connector 46 to the connector mount 44. The tab 44 may be configured to be carried by the connector mount 44 in an operative attachment. In some implementations, an individual tab 44 may be substantially L-shaped, as shown in FIG. 7.

In some implementations, the tab 44 may include a layer of adhesive (not shown in FIG. 1, FIG. 7, and FIG. 8), and/or other components. A layer of adhesive may be coupled to and/or incorporated with a surface (e.g., a surface that comes into contact with the contact surface 30 of the mandibular portion 28). Adhesives and/or other components may be configured to facilitate operatively attachment of the tab 44 to the mandibular portion 28 and/or maxillary portion 12. The tab 44 may include a backing (not shown in FIG. 1, FIG. 7, and FIG. 8) that may be removed to expose an adhesive. In some implementations of the tab 44 including an adhesive layer, the slot 52 may or may not be omitted. For example, if the slot 52 is omitted, the tab 44 may need not be carried by the connector mount 44. Instead, the tab 44 may be adhered to the mandibular portion 28 and/or maxillary portion 12 as needed.

In some implementations, the slot 52 may be configured to have a predetermined length. The slot 52 may be configured such that the tab 44 may be attached to the connector mount 40 with minimal force by a user. By way of non-limiting example, the slot 52 may be formed in accordance with a known or standardized width of the connector mount 40. In some implementations, the slot 52 may have a length that is less than a known width of the connector mount 40. For example, a user (e.g., a dental practitioner and/or other user) may form the slot 52 to a desired length (e.g., by cutting, sanding, scraping, and/or other slot forming techniques) such that the tab 44 may fit over the connector mount 40 with minimal force applied by the user. In some implementations, the slot 52 may have a length that is equal to or slightly less than a known width of the connector mount 44. By way of non-limiting example, the slot 52 may be configured such that the tab 44 may be carried in a frictional engagement by the connector mount 44 that may require at least some applicative force by a user to slide the tab 44 into its operative engagement with the connector mount 40.

Referring now to FIG. 1, in some implementations, a given tab 44 may have a predetermined thickness "T" that may provide a predetermined displacement of the mandibular portion 28 relative the maxillary portion 12 (e.g., a VDO) when the device 10 is in an as-used position in the mouth of the subject. For example, in some implementations, the thickness "T" may be in the range of 0.1 to 10, and/or other ranges. In some implementations, the thickness "T" may be in the range of 0.5 to 3 millimeters, and/or other ranges. In some implementations, the thickness "T" of the tab 44 may be 1 millimeter and/or other thickness.

In some implementations, the connector mounts 40 may be configured to receive multiple tabs 44 in a stacked arrangement carried by a given connector mount 40. A user may selectively employ one or more given tabs 44 with the device 10 based on a given thickness of a single tab 44 and/or a cumulative thickness of multiple tabs 44. One or more methods of treating a subject suffering from sleep apnea by modifying an oral appliance that may be formed the same or similar to device 10 are described in more detail herein.

Figure 9:
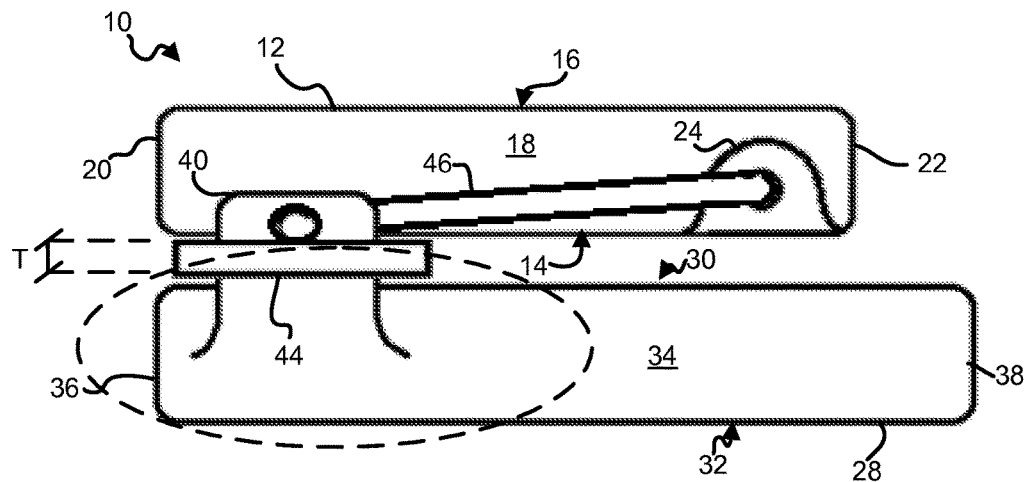
FIG. 9 illustrates an assembled side view of the device of FIG. 1, in accordance with one or more implementations.

In some implementations, the tab 44 may include one or more of a protruding contact portion 54 and/or other components. A protruding contact portion 54 may be configured for operative positioning between the contact surface 14 of the maxillary portion 12 and the contact surface 30 of the mandibular portion 28, as shown in FIG. 9. In some implementations, the tab 44 may be configured such that the contact portion 54 may be positioned at or near the molars and/or other teeth of the subject when the device 10 is in the as-used position (an approximate area where the molars may be positioned is shown by the dashed ellipse). Operative positioning of the contact portion 54 within the area of dashed ellipse and/or other area may provide improved comfort to the wearer.

Figure 10:
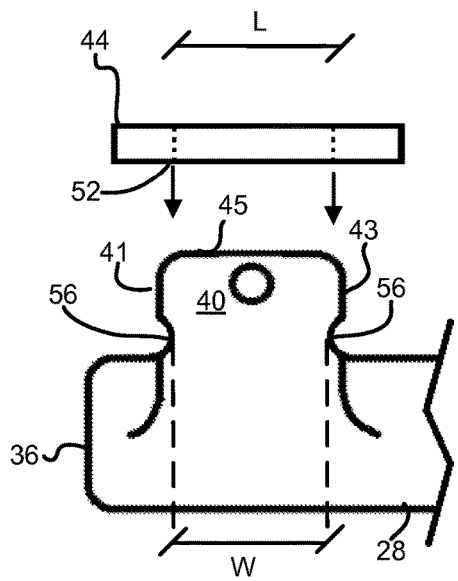
FIG. 10 illustrates a partial side view of a connector mount, in accordance with one or more implementations.
Figure 11:
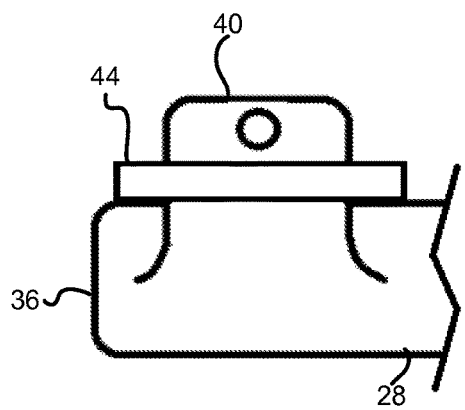
FIG. 11 shows a view of the connector mount as illustrated in FIG. 10 with a given tab in a seated attachment on the connector mount, in accordance with one or more implementations.

FIG. 10 and FIG. 11 illustrate an implementation of the device 10 configured to facilitate a seated attachment of the tabs 44 to the connector mounts 40. By way of non-limiting example, a seated attachment may correspond to a "snap fit" type attachment and/or other types of attachment. A given connector mount 40 may include one or more of one or more detents 56 (e.g., one detent 56 and/or two opposing detents 56 as shown) disposed on one or more side edges (e.g., a first side edge 41 and/or second side edge 43) of a connector mount 40 and/or other components. In some implementations, the detents 56 may form a width "W" of the connector mount 40. The width "W" associated with the detents 56 may be less than a width associated with a distal end 45 of the connector mount 40. In some implementations, the width "W" may be formed to be the same or similar to a length "L" of the slot 52 (shown in dashed lines) formed in a given tab 44. Due to the malleability of the material forming the connector mount 40 and/or the distal end 45, the distal end 45 may deflect as the tab 44 is slid over the connector mount 40 to compensate for the lesser width of the slot 52 until the slot 52 is seated over the detents 56 (e.g., the tab 44 snap-fits onto the connector mount 40). In some implementations, the width W and length L may be standardized lengths. Such standardization may allow for different devices that have varying geometries of the mandibular portion 28 and/or maxillary portion 12 and/or other oral appliances having connector mounts the same or similar as those shown, to commonly employ the tabs 44 of the presented invention.

Figure 12:
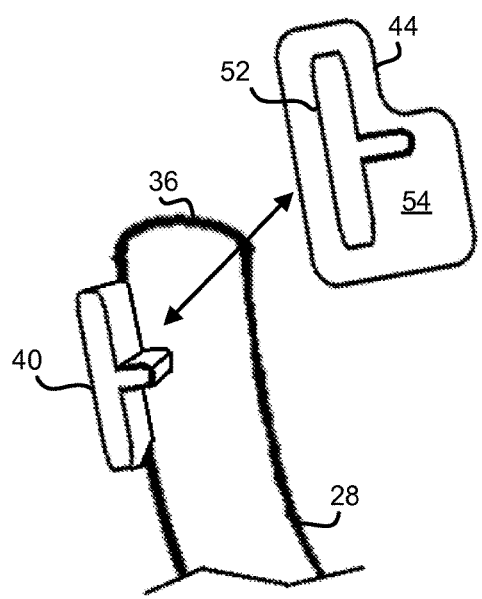
FIG. 12 illustrates a top view of a connector mount of a mandibular portion of the device of FIG. 1 formed with a substantially T-shaped cross section, in accordance with one or more implementations.

FIG. 12 illustrates an implementation of the device 10 wherein the connector mounts 40 of the mandibular portion 28 may be formed having a non-linear cross section. For example, a given connector mount 44 may have a substantially T-shaped cross section, and/or other non-linear cross section (e.g., curved, star shaped, and/or other shapes). In the implementation shown, the tabs 44 of the device 10 may be formed having a slot 52 being similarly shaped to the cross-section of the connector mount 40. For example, the slot 52 may be a T-shaped slot and/or other shaped slot configured to match the T-shaped cross-section and/or other shape cross-section of the connector mount 40. The non-linear cross section of the mount 44 and/or matching shape slot 52 may be configured to facilitate operative mounting of the tab 44 to the connector mount 40 with the tab 44 and/or connector mount 40 registered in positions in accordance with the corresponding shapes. As such, forming of the slot 52 and connector mount 40 to have non-linear cross sections may ensure that the tab 44 may be in a particular registration orientation for operative mounting to the connector mount 40 (e.g., to ensure the slot 52 and connector mount 40 are correctly aligned). This may further ensure that the contact portion 54 may be positioned in a desired location and/or orientation between the contact surfaces (30, 14) of the mandibular portion 28 and maxillary portion 12. By way of non-limiting example, this may ensure that the contact portion 54 is properly located over the molars and/or other teeth of a subject. It is noted that the T-shaped cross sections as currently shown are for illustrative purposes only and is not intended to be limiting. In other implementations, the connector mounts 40 and/or slots 52 of the tabs 44 may be formed having other shapes and/or cross sections.

Figure 13:
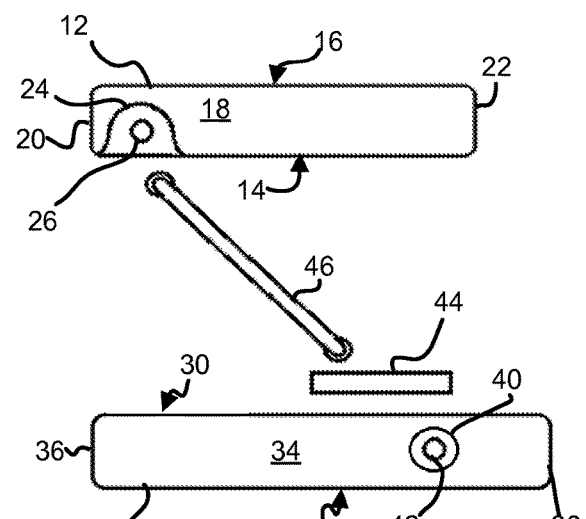
FIG. 13 illustrates an exploded side view of a device for providing a measured vertical dimension of occlusion, in accordance with one or more implementations.
Figure 14:
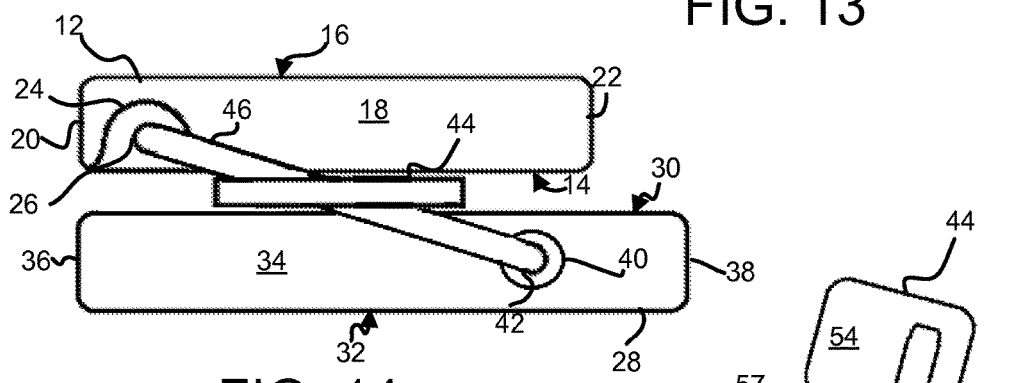
FIG. 14 shows an assembled side view of the device of FIG. 13, in accordance with one or more implementations.
Figure 15:
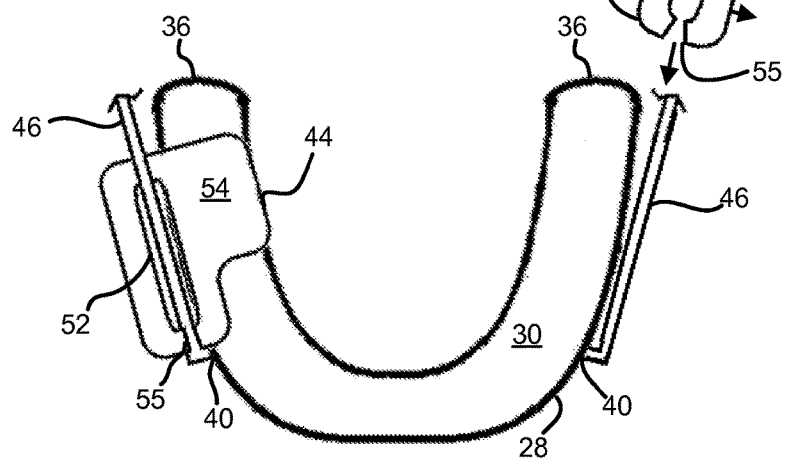
FIG. 15 shows a top view of a mandibular portion of the device of FIG. 13, in accordance with one or more implementations.

FIG. 13, FIG. 14, and FIG. 15 illustrate an implementation of the device 10 wherein the connector mounts 40 of the mandibular portion 28 may be positioned on opposing sides of the outer sidewall 34 at or near the distal end 38, and/or the connector mounts 24 of the maxillary portion 12 may be positioned on opposing sides of the outer sidewall 18 at or near the proximal ends 20. The current implementation facilitates a technique in which mandibular advancement may be accomplished, e.g., the connection of the mandibular portion 28 with the maxillary portion 12 via the connector 46 that positions the mandibular portion 28 forward of the maxillary portion 12. In the implementation shown, the connector mounts 40 of the mandibular portion 28 may be formed into the outer sidewall 34 as a uniform object. The connector mounts 24 of the maxillary portion 12 may similarly be formed in the outer sidewall 18.

The connector mounts 24, 40 may include receiving apertures 26, 42, respectively, configured to attach to ends of the connector 46. For example, the ends of the connector 46 may include pins with flanged ends and/or other components. In some implementations, other techniques for attaching the ends of the connector 46 to the connector mounts 24, 40 may be employed. For example, the ends of the connector 46 may be attached to the connector mounts 26, 40 using screws and/or other fasteners. In the some implementations, the tabs 40 may be carried by the connectors 46. For example, the connectors 46 may extend through the slots 52 of the tabs 44 so as the contact portions 54 are substantially positioned at or near the proximal ends 36 as illustrated in FIG. 15.

Referring to FIG. 15, in some implementations, a first end 57 of a given tab 44 may include a slit 55 and/or other components. The slit 55 may communicate through a side edge of the tab 44 to the slot 52. The slit 55 may be configured to facilitate splaying of the first end 57 by the user. In some implementations, the given tab 44 may be configured to attach to the connectors 46 by splaying the first end 57. Splaying the first end 57 may expose the slot 52 such that the connector 46 may be communicated through the slit 55 and into an operative positioning on the device 10. The provision of a slit 55 on a given tab 44 may alleviate the need to detach the connectors 46 from the mandibular portion 28 and/or maxillary portion 12 and feed the connectors 46 through the slot 52 to achieve the operative attachment thereof.

In some implementations, a slit 55 may have a width that is less than the width of a given connector 46. In some implementations, the width of the slit 55 may gradually taper from a first end at its widest opening (adjacent the side edge of the tab 44) to a second end at its narrowest opening (adjacent the slot 52). In some implementations, the widest opening may be substantially equal to the width of the connector 46 while the narrowest end may be substantially less than the width of the connector 46. As such, the tapered slit 55 may assist the user in guiding the tab 44 in its engagement with the connector 46. A tapered slit 55 may further be configured to provide a type of "snap fit" attachment of the tab 44 to a connector 46. It is noted that the implementation of the tab 44 shown in FIG. 15 may be employed with one or more of the implementations of the device 10 described herein and should not be considered limited by the depiction in FIG. 15.

Figure 16:
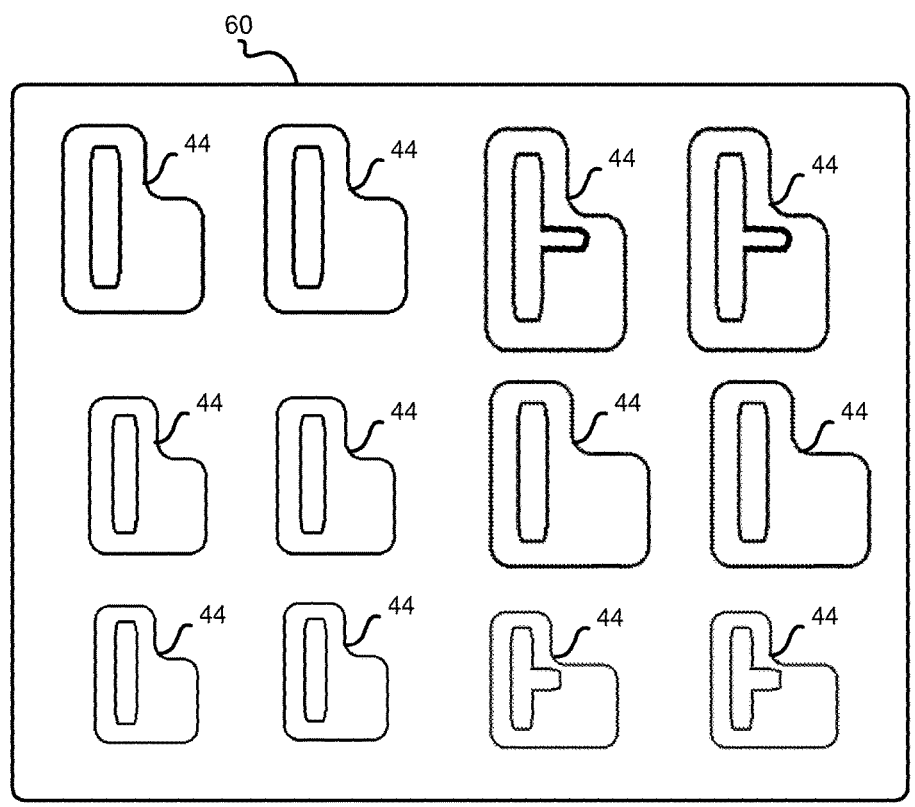
FIG. 16 illustrates a kit of tabs configured to provide a measured VDO in an oral appliance, in accordance with one or more implementations.

FIG. 16 illustrates an implementation of a kit 60 comprising one or more tabs 44 for use with the device 10 and/or other oral appliances. In some implementations, the kit 60 may include one or more tabs 44 and/or other components. Individual tabs 44 may vary by one or more of thickness, size, dimension, configuration, slot length, slot width, slot shape, contact portion dimensions, contact portion surface area, color, and/or other variances.

By way of non-limiting example, tabs of a common thickness, size, dimension, configuration, slot length, slot width, slot shape, contact portion dimensions, contact portion surface area and/or other aspect may be color coded to a similar color for easy recognition of like tabs. By way of non-limiting example, individual tabs of a first thickness may be a first color while individual tabs of a second thickness may be a second color different from the first color. Thicknesses of one or more tabs may be distinguishable from thicknesses of one or more other tabs based on the assigned color. In some implementations, a reference chart may be provided to a user that may describe a color-to-thickness relationship. In some implementations, a prescribed thickness of a given tab may be provided as indicia imparted on at least one surface of the given tab. In some implementations, tabs sharing a common thickness and/or other common configuration may be provided in the kit 60 in pairs and/or other quantities.

In some implementations, the kit 60 may include one or more mandibular portions 28 (not shown in FIG. 16), one or more maxillary portions 12 (not shown in FIG. 16), one or more connectors 46 (not shown in FIG. 16), and/or other components. In some implementations, the kit 60 may include one or more tabs 44 that may be of the same or substantially the same thickness, size, dimension, configuration, slot length, slot width, slot shape, contact portion dimensions, contact portion surface area, and/or other similarities.

In some implementations, the kit 60 may be provided in a sterile packaging, and/or other types of packaging. In some implementations, the kit 60 may be provided to a user that allows the user to selectively employ the desired tabs 44 as needed for treatment of sleep apnea of a subject and/or for other purposes. In some implementations, the kit 60 may be provided as part of a therapy regime. For example, a method of treating sleep apnea by providing VDO with an oral appliance may include steps for modifying a measured amount of VDO by selectively interchanging, shacking, and/or otherwise employing one or more tabs 44 during predetermined periods of use of the oral appliance (e.g., such as the device 10).

Figure 17:
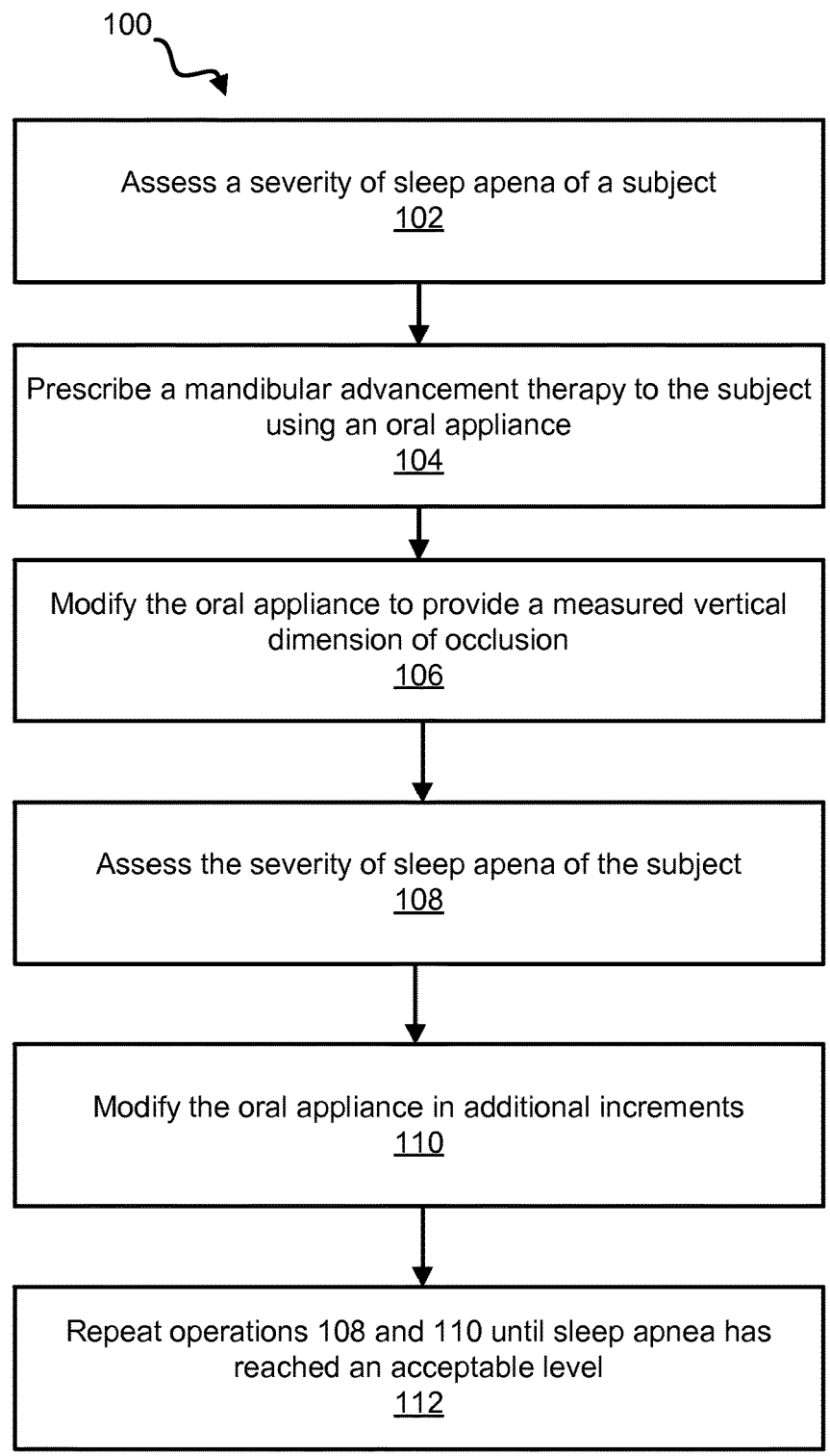
FIG. 17 illustrates a method of providing VDO in an oral appliance used for the treatment of sleep apnea, in accordance with one or more implementations.

FIG. 17 illustrates a method 100 of providing a measured VDO in a subject using an oral appliance, in accordance with one or more implementations. The operations of method 100 presented below are intended to be illustrative. In some embodiments, method 100 may be accomplished with one or more additional operations not described, and/or without one or more of the operations discussed. Additionally, the order in which the operations of method 100 are illustrated in FIG. 17 and described below are not intended to be limiting. In some implementations, method 100 may be implemented at least in part using one or more tabs the same or similar to the tabs 44 employed in the device 10 and/or other components of the device 10 shown and describe herein.

Referring now to method 100 in FIG. 17, at an operation 102, an assessment of a severity of sleep apnea of a subject may be performed. In some implementations, the assessment may be performed using a validated sleep testing device and/or other components and/or techniques. For example, a home sleep testing device may comprise a device provided by Res Med, called the Apnea Link®, and/or other devices may be employed. By way of non-limiting example, an assessment may be performed using one or more devices employed for clinical studies such as full laboratory based polysomnography, the Watch PAT device provided by Itamar Inc. and/or other devices. In some implementations, an assessment may be performed to determine an amount of apneic events per hour that are experienced by the subject, and/or may determine other information.

In some implementations, assessment of the severity of sleep apnea may be performed by taking X-rays of a subject and/or evaluating a position of a hyoid bone. In particular, as the hyoid moves superiorly, the tongue may moves superiorly as well. Such movement may result in a crowding in the oral cavity and/or a positive impact upon the apnea-hypopnea index of the subject. With each addition of vertical spacing the posterior airway space adjacent the hyoid bone may be measured to provide different iterations of assessment.

In some implementations, treatment of sleep apnea may aim to reduce an occurrence of apneic events experienced by the subject and/or to reduce a degree of oxygen desaturation associated with apneic events. In some implementations, a sleep test may be used to determine an "untreated" or baseline amount of apneic events experienced by the subject and/or a degree of oxygen desaturation. Therapy may be applied in a manner which aims to reduce the amount of apneic events to an acceptable level. The acceptable level may vary from subject to subject. In some implementations, a reduction of 50% or more from the baseline amount of apneic events may be considered an acceptable level. However, depending on the subject's severity, a reduction of less than 50% may be considered successful treatment. In some implementations, the acceptable level of apneic events in a subject may be at or below 10 events per hour and/or other amount. By way of non-limiting example, an acceptable level may be between 5 and 15 events per hour, and/or other ranges. It may be recommended that, in healthy individuals, a level of hypoxemia should not drop below 90% O2 saturation of blood for more than 1% of the night while sleeping.

In some implementations, a device-implemented assessment may be accompanied by a questionnaire, and/or interview conducted with the subject. The interview and/or questionnaire may include questions such as "Do you snore?", "Do you feel sleepy/tired during the day?", "Do you awaken several times during the night?", and/or other questions used for purpose of assessing the severity of sleep apnea in a subject. The questionnaire and/or interview may further aid a practitioner in assessing the severity of sleep apnea of the subject.

At an operation 104, based on the assessment performed at operation 102, a mandibular advancement therapy regime may be prescribed for the subject. For example, the therapy regime may be associated with the use an oral appliance configured to provide mandibular advancement of the subject and/or other types of treatment. In some implementations, the therapy regime may be prescribed that includes an oral appliance having one or more of a maxillary portion, a mandibular portion, and/or one or more connectors that may be the same or similar to the maxillary portion 12, the mandibular portion 28, and/or the connectors 46 (shown in FIGS. 1-15 and described herein), and/or other components.

Oral appliances for mandibular advancement may increase pharyngeal width at all levels in both the upright and supine positions. In some implementations, the use of an oral appliance for mandibular advancement may shorten the distance between the mandible and hyoid bone compared to when it is not used (which may be evaluated, for example, using X-rays of the subject). A reduction in distance between the mandible and hyoid bone may be a critical area to assess during treatment. For example, if the subject is not responding optimally to the mandibular advancement treatment, the hyoid bone may need to be taken into consideration. As a solution described herein, augmenting a VDO in the oral appliance may create more space for the tongue and enable a larger airway dimension.

In some implementations, the mandibular advancement therapy regime may include instructing the subject to wear the oral appliance for one or more nights. The mandibular advancement provided by the oral appliance may be at an initial displacement during a first night. The mandibular advancement may be adjusted (e.g., increased, decreased, and/or adjusted in other ways) upon each successive night, in amounts depending on the therapy as prescribed by a practitioner.

By way of non-limiting example, a first night of wearing the oral appliance may include providing a connector that provides a mandibular advancement of 1 millimeter and/or other amount. Successive nights may include increasing the displacement. This may be performed up until no appreciable improvement in the sleep apnea of the patient may be seen and/or until a maximum tolerance for the displacement is reached (e.g., based on comfort and/or other factors). For example, a maximum tolerance of mandibular advancement may be from 5 to 15 millimeters, and/or other ranges. When maximum tolerance is reached, and/or when no appreciable improvement in sleep apnea using mandibular advancement techniques may be seen (e.g., no reduction of the occurrence of apneic events per hour), application of VDO may be provided using the oral appliance. For example, additional sleep tests may be conducted during the therapy to determine whether there is a decrease in apneic events and/or oxygen desaturation while using the oral appliance. The sleep test may comprise, for example, application of a sleep test device, a questionnaire and/or interview conducted with the subject, and/or other devices and/or techniques. Other tests may be employed where the position of the hyoid bone may be assessed.

At an operation 106, in response to determining that no appreciable improvement in sleep apnea is seen through mandibular advancement and/or the subject has reached their maximum mandibular advancement tolerance, the oral appliance may be modified to include VDO. The modification of the oral appliance may be accompanied by one or more nights of sleep testing. For example, the number of apneic events, amount of oxygen desaturation, and/or position of the hyoid bone may be assessed over the one or more nights of sleep testing.

In some implementations, a subject may be provided an oral appliance configured to provide VDO, and/or the oral appliance used for mandibular advancement may be modified to provide a measured VDO. By way of non-limiting example, during a first night, the oral appliance may be modified and/or otherwise configured to provide a 1 to 3 millimeter, and/or other ranges, of VDO. By way of non-limiting example, a female subject may be prescribed 1 millimeter (or other amount) of VDO on a given night of therapy. By way of non-limiting example, a male subject may be prescribed a 2 millimeter (or other amount) of vertical dimension of occlusion on a given night of therapy.

In some implementations, during a second night of modifying the oral appliance associated with operation 106, the oral appliance may be further modified and/or otherwise configured to provide an additional 1-2 millimeters (and/or other range) of VDO. Modification may include one or more of adding tabs in stacked arrangements, interchanging tabs with tabs of greater thickness, and/or may include one or more other types of modifications. By way of non-limiting example, a female subject may be prescribed an additional 1 millimeter (or other amount) of VDO using the oral appliance on a second night (e.g. with a total of 2 millimeters and/or other amounts). As another non-limiting example, a male subject may be prescribed an additional 1 millimeter (or other amount) of VDO using the oral appliance on a second night (e.g., with a total of about 3 millimeters and/or other amounts).

In some implementations, operation 106 may be performed using one or more tabs the same or similar to tabs 44 (shown in FIG. 1, FIGS. 7-16 and described herein). In some implementations, operation 106 may be performed using a device the same or similar to the device 10 (shown in FIGS. 1-16 and described herein).

At an operation 108, results of the sleep tests performed during the application of VDO (e.g. over two nights as presented, and/or other durations) may be evaluated to determine if there may be improvements in sleep apnea of the subject. In some implementations, operation 108 may be performed using a sleep testing device and/or other devices and/or techniques. In some implementations, operation 108 may be performed using techniques for assessing the position of the hyoid bone and/or techniques.

By way of non-limiting example, determinations of improvement may include determining one or more of if the amount of apneic events has reduced down to an acceptable level for the subject; oxygen desaturation has reduced down an acceptable level for the particular subject, and/or other operations.

In some implementations, assessing a position of the hyoid bone may provide insights into an amount of opening of an airway (e.g., posterior airway space) of the subject. The amount of opening may indicate one or more of a successful treatment, a need to provide additional VDO, and/or other outcomes. By way of non-limiting example, a measure of a posterior airway space may be taken at intervals of the modifications to the VDO provided by the oral appliance. In some implementations, 9 to 13 millimeters and/or other ranges of hyoid elevation may be achieved with one or more of mandibular advancement in the range of 2 to 4 millimeters and/or other ranges, a vertical dimension in the range of 1 to 15 millimeters and/or other ranges, and/or other applications of therapy.

At an operation 110, additional modification to the oral appliance may be provided. For example, over one or more additional nights of employing the modified oral appliance, additional 0.5 to 1 millimeter (and/or other ranges) increments of VDO may be provided. In some implementations, operation 110 may be performed using one or more tabs the same or similar to tabs 44 (shown in FIG. 1, FIG. 7-16 and described herein) and/or other components. In some implementations, operation 110 may be performed using a device the same or similar to the device 10 (shown in FIGS. 1-16 and described herein), and/or other components.

At an operation 112, one or both of operations 108 and/or 110 may be repeated one or more times. In some implementations, operations 108 and/or 110 may be repeated until a target result may be obtained. A target result may correspond to one or more of apneic events per hour meeting and/or beating an acceptable level for a given subject, oxygen saturation being at an acceptable for a given subject, posterior airway space being at an acceptable level for the given subject, the subject reaching their maximum comfortable jaw position, and/or other results. The determination of the subject reaching their maximum comfortable jaw position may be determined subjectively through interviewing the subject, through participation of the subject in a questionnaire, and/or by other techniques.

In some implementations, a method of improving comfort in a patient employing an oral appliance may be accomplished using one or more tabs 44 and/or other components of the device 10 as presented herein, and/or other components. For example, after prescribing a subject to a mandibular advancement therapy using an oral appliance, an assessment of the comfort level of the subject may be performed. Several types of complaints may be alleviated by adding VDO to their appliance. For example, subjects may suffer discomfort due to one or more of pain in one or both sides of the temporomandibular joint areas; pain in one or more teeth, most likely due to clenching, bruxism and/or other issues; soreness in the tongue and/or inner cheek surfaces; and/or other comfort issues. In one or more scenarios, as well as during an occurrence of other issues, the oral appliance may be modified by adding 1-5 millimeters (and/or other amounts) of VDO. For example, the oral appliance may be modified to include 3 millimeters and/or other amounts of VDO. Generally, if pain is mild, the subject may be prescribed to employ a modified VDO immediately (e.g., the same night). If pain is moderate or more, the subject may be instructed to discontinue using their appliance for 3 days (and/or other amount of days) before wearing a modified appliance. At a subsequent contact by a dental practitioner with the subject (e.g., a few days, weeks, or months later), a subsequent assessment of the comfort level of the subject may be evaluated. In some implementations, if the subject continues to experience pain (e.g., improved, but pain may be lingering), the oral appliance may be further modified to include an additional 0.5-2 millimeters of VDO and/or other ranges. The operations of assessing comfort and/or adding additional increments of VDO may be repeated until maximum conform may be achieved.

Although the present technology has been described in detail for the purpose of illustration based on what is currently considered to be the most practical and preferred implementations, it is to be understood that such detail is solely for that purpose and that the technology is not limited to the disclosed implementations, but, on the contrary, is intended to cover modifications and equivalent arrangements that are within the spirit and scope of the appended claims. For example, it is to be understood that the present technology contemplates that, to the extent possible, one or more features of any implementation can be combined with one or more features of any other implementation.

What is claimed is:

1. An oral appliance device configured to provide a measured vertical dimension of occlusion, the oral appliance device comprising:
    a maxillary portion having an upper cavity configured to receive one or more maxillary teeth of a subject in an as-used position of the oral appliance device inserted in the mouth of the subject;
    a first mount disposed on the maxillary portion;
    a mandibular portion having a lower cavity configured to receive one or more mandibular teeth of the subject in the as-used position;
    a second mount disposed on the mandibular portion, the second mount forming a wing extending from an outer wall of the mandibular portion toward the maxillary portion;
    one or more connectors, individual ones of the connectors having an end configured to be attached to the maxillary portion and another end configured to be attached to the mandibular portion, wherein the one or more connectors are configured to advance the mandibular portion forward of the maxillary portion to provide mandibular advancement of the subject when the oral appliance device is in the as-used position, the one or more connectors including a first connector, the first connector comprising a first end configured to attach to the maxillary portion, and a second end configured to attach to the mandibular potion;
    one or more tabs configured to be positioned between respective contact surfaces of the mandibular portion and the maxillary portion, individual ones of the tabs being formed with a thickness that provides a predetermined displacement of the mandibular portion from the maxillary portion, the one or more tabs including a first tab;
    wherein the one or more tabs positioned between the maxillary portion and the mandibular portion are configured to provide a non-zero vertical dimension of occlusion in the subject with the oral appliance device in the as-used position;
    wherein the first mount is configured to facilitate attachment of the first end of the first connector to the maxillary portion;
    wherein the second mount is configured to facilitate attachment of the second end of the first connector to the mandibular portion; and
    wherein the first tab comprises a slot, the slot having a shape that is complementary to a shape of the wing formed by the second mount such that the first tab is configured for attachment to the second mount by inserting the wing into the slot of the first tab, wherein the attachment of the first tab to the second mount is independent from the attachment of the second end of the first connector to the second mount.

2. The oral appliance device of claim 1, wherein individual tabs further comprise a contact portion, the contact portion being configured to engage at least a part of the contact surface of one or both of the mandibular portion or the maxillary portion, the at least part of the contact surface corresponding to a location of molars of the subject when the oral appliance device is in the as-used position.

3. The oral appliance device of claim 1, wherein the first tab further comprises a slit disposed at a side edge of the first tab, the slit communicating with a slot, the slit being configured to facilitate attachment of the first tab to the first connector independently from the attachment of the first connector to the second mount.

4. The oral appliance device of claim 3, wherein the slit tapers in width from a third end of the slit adjacent the side edge of the first tab to a fourth end of the slit adjacent the slot, the third end being wider than the fourth end.

5. The oral appliance device of claim 2, wherein individual tabs are further configured such that the contact portion of a given tab further comprises an adhesive, the adhesive being configured to facilitate the engagement to the at least part of the contact surface of one or both of the mandibular portion or the maxillary portion.

\* \* \* \* \*